US007276690B1

(12) United States Patent
Lorusso et al.

(10) Patent No.: US 7,276,690 B1
(45) Date of Patent: *Oct. 2, 2007

(54) METHOD AND SYSTEM FOR E-BEAM SCANNING

(75) Inventors: Gian Francesco Lorusso, Fremont, CA (US); Luca Grella, Gilroy, CA (US); Douglas K. Masnaghetti, San Jose, CA (US); Amir Azordegan, Santa Clara, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/911,216

(22) Filed: Aug. 4, 2004

Related U.S. Application Data

(63) Continuation of application No. 10/426,665, filed on Apr. 30, 2003, now Pat. No. 6,815,675.

(51) Int. Cl.
*G01N 23/00* (2006.01)

(52) U.S. Cl. .................... 250/307; 250/398; 250/310

(58) Field of Classification Search ............... 250/307
See application file for complete search history.

(56) References Cited

U.S. PATENT DOCUMENTS 5,302,828 A * 4/1994 Monahan .................... 250/307
2001/0006216 A1 * 7/2001 Koike ........................ 250/398

FOREIGN PATENT DOCUMENTS

JP 09-180667 * 11/1997
JP 2001-006599 * 12/2001

* cited by examiner

*Primary Examiner*—Jack I. Berman
*Assistant Examiner*—Phillip A. Johnston
(74) *Attorney, Agent, or Firm*—Okamoto & Benedicto LLP

(57) ABSTRACT

The disclosure relates to a method and system of electron beam scanning for measurement, inspection or review. In accordance with one embodiment, the method includes a first scan on a region to collect first image data. The first image data is processed to determine information about a feature in the region. A scanning method is selected for imaging the feature. A second scan using the selected scanning method on the feature is then applied to collect second image data.

7 Claims, 20 Drawing Sheets

(a) perpendicular (b) parallel

FIG. 2

METHOD AND SYSTEM FOR E-BEAM SCANNING

CROSS-REFERENCE TO RELATED APPLICATIONS

The present application is a continuation of U.S. patent application Ser. No. 10/426,665, filed Apr. 30, 2003 now U.S. Pat. No. 6,815,675, by inventors Gian Francesco Lorusso; Luca Grella; Douglas K. Masnaghetti; and Amir Azordegan, and entitled "Method and System for E-Beam Scanning," the disclosure of which is hereby incorporated by reference.

BACKGROUND OF THE INVENTION

1. Field of the Invention

The present invention relates to scanning electron beam apparatus and methods of using scanning electron beam apparatus.

2. Description of the Background Art

As technology progresses in the semiconductor industry, the features of integrated circuit devices are being reduced to smaller and smaller sizes. Such reduction in feature size enables a greater density of devices to be manufactured on a semiconductor. However, increasingly smaller feature sizes require increasingly higher resolutions and accuracy in measurement, inspection, and review equipment.

One category of such equipment is based on scanning electron microscope (SEM) technology. In an SEM, a beam of electrons (an electron beam or e-beam) is scanned over a specimen, and the resulting electrons that are returned from the specimen surface are used to create an image of the specimen surface, or to acquire a linescan. In order to handle increasingly smaller feature sizes, it is desirable to increase the effective resolution (i.e. the apparent beam width) and/or accuracy of SEM-based equipment used for feature measurement, substrate inspection, or defect review.

SUMMARY

The invention relates to a method and system for electron beam scanning for measurement, inspection or review.

In accordance with one embodiment of the invention, the method includes a first scan on a region to collect first image data. The first image data is processed to determine information about a feature in the region. A scanning method is selected for imaging the feature. A second scan using the selected scanning method on the feature is then applied to collect second image data.

In accordance with another embodiment of the invention, the method includes scanning at least one unit of pixels to collect image data. A delay period is then inserted to reduce an electron dosage to the substrate. These steps are repeated.

In accordance with another embodiment of the invention, the method includes scan lines that converge upon a feature on the substrate. The scan lines may be linear (and oriented either in one or two dimensions) or may be shaped in dependence upon a shape of a feature of interest.

In accordance with another embodiment of the invention, the method includes randomly ordered scan units. The randomly ordered scan units may either be randomly ordered scan lines or randomly ordered pixels.

In accordance with another embodiment of the invention, the method includes scan lines proceeding bi-directionally. The scan lines may proceed bi-directionally in one dimension or in two dimensions.

Another embodiment relates to a system for electron beam scanning. The system may include the following: means for a first scan on a region to collect first image data; means for processing the first image data to determine information about a feature in the region; means for selecting a scanning method for imaging the feature; and means for a second scan using the selected scanning method on the feature to collect second image data.

BRIEF DESCRIPTION OF THE DRAWINGS

FIG. 2 compares simulated and experimental images under the two different scanning methods.

DETAILED DESCRIPTION

Applicants have determined that the effective resolution obtainable from a scanning electron beam apparatus can depend upon the orientation of the scan lines with respect to a feature being imaged. In particular, when the scan lines are perpendicular to the feature edge, the edge appears disadvantageously broader (more blurred). On the other hand, the edge of the feature appears advantageously narrower (less blurred) when the scan lines are parallel to the feature edge.

Figure 1:
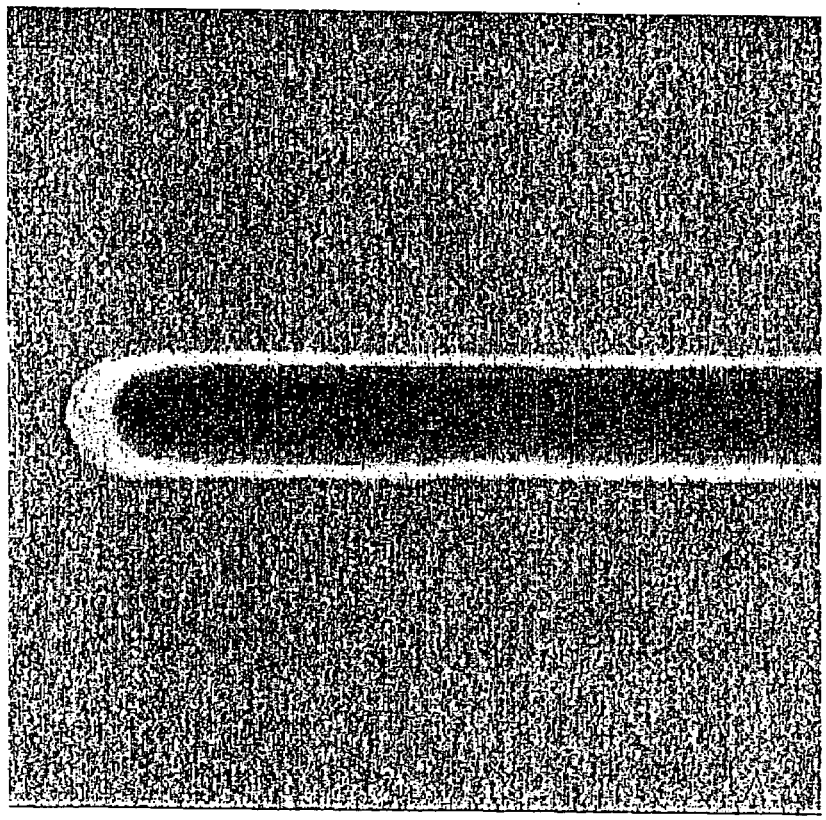
FIG. 1 compares experimental images of a same feature under two different e-beam scanning methods.
Figure 1:
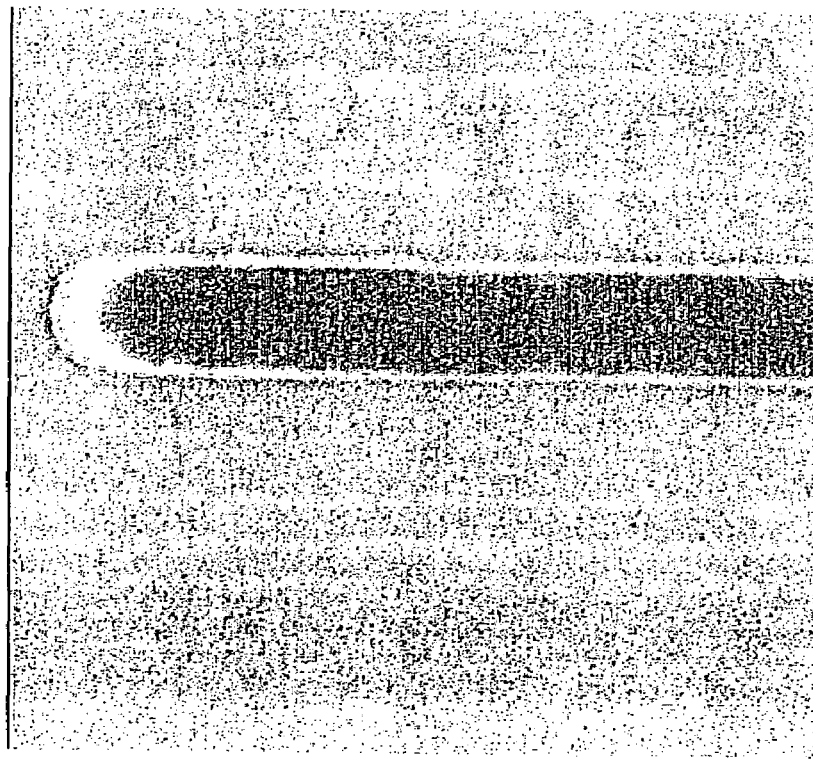

FIG. 1 compares experimental images of a same feature under two different e-beam scanning methods. The left image (a) shows a vertical feature that is scanned with horizontal scan lines. In other words, the image is scanned with the electron beam tracing one horizontal line, then a next horizontal line, then a next horizontal line, and so on. Since the feature's primary edges and the scan lines are perpendicularly oriented against each other, the left image (a) shows an example of "perpendicular scanning" or "orthogonal scanning."

On the other hand, the right image (b) shows a vertical feature that is scanned with vertical scan lines. In other words, the image is scanned with the electron beam tracing one vertical line, then a next vertical line, then a next vertical line, and so on. Since both the feature's primary edges and the scan lines are vertical, the right image (b) shows an example of "parallel scanning."

By comparing the images, one can see that the feature's vertical edges appear narrower under the (b) parallel scanning and broader under the (a) perpendicular scanning. In other words, there is advantageously less blurring when the scan lines are oriented to be parallel to the feature of interest.

Figure 2:
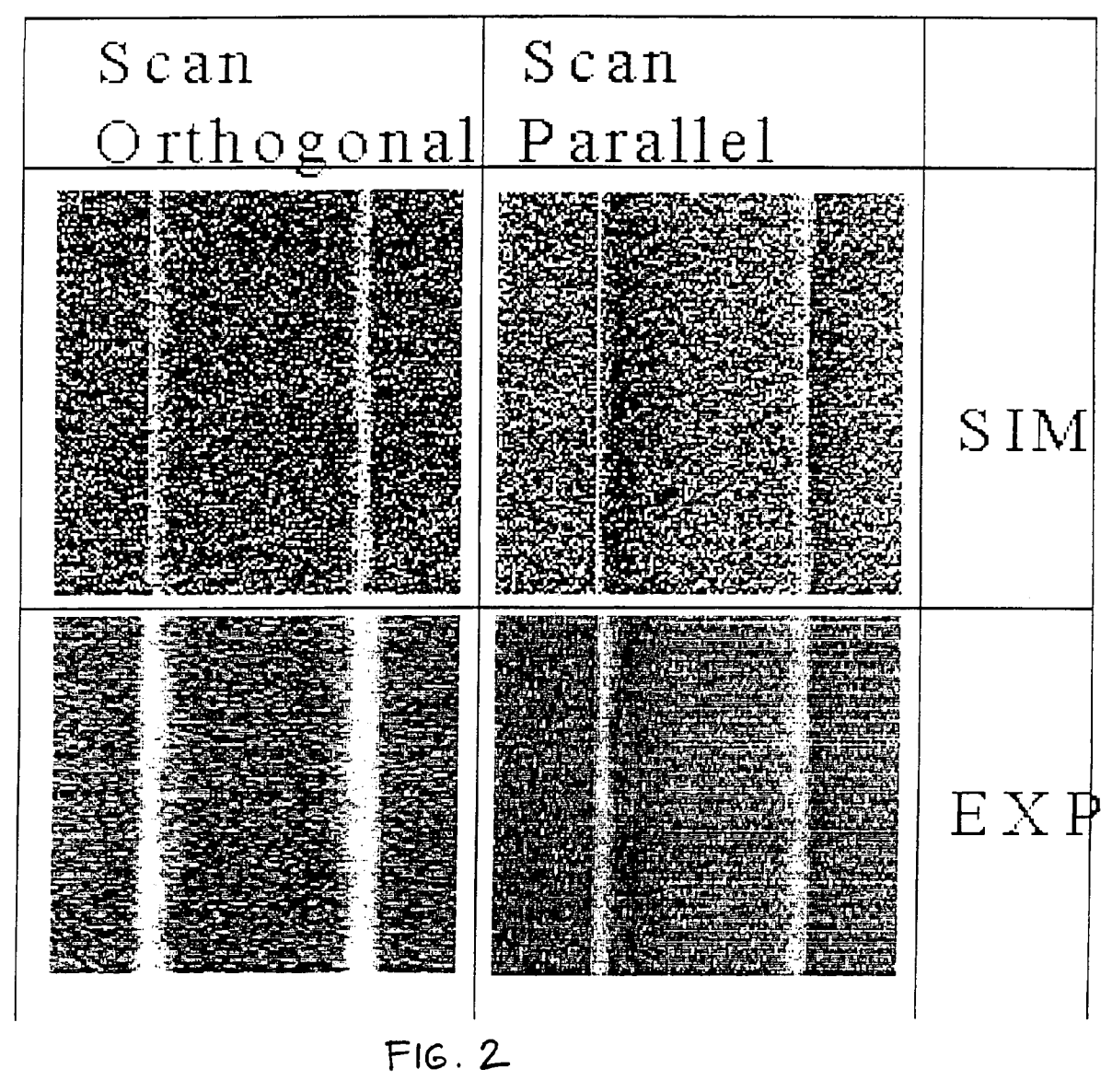

FIG. 2 compares simulated and experimental images under the two different scanning methods. The top row shows two simulated (SIM) images from theoretical physical calculations, and the bottom row shows two experimental (EXP) images. The left two images are derived using orthogonal (perpendicular) scanning, and the right two images are derived using parallel scanning. As shown in FIG. 2, the simulated images confirm what is seen in the experimental images. In both simulated and experimental images, the parallel scanning results in less edge blurring.

Figure 3A:
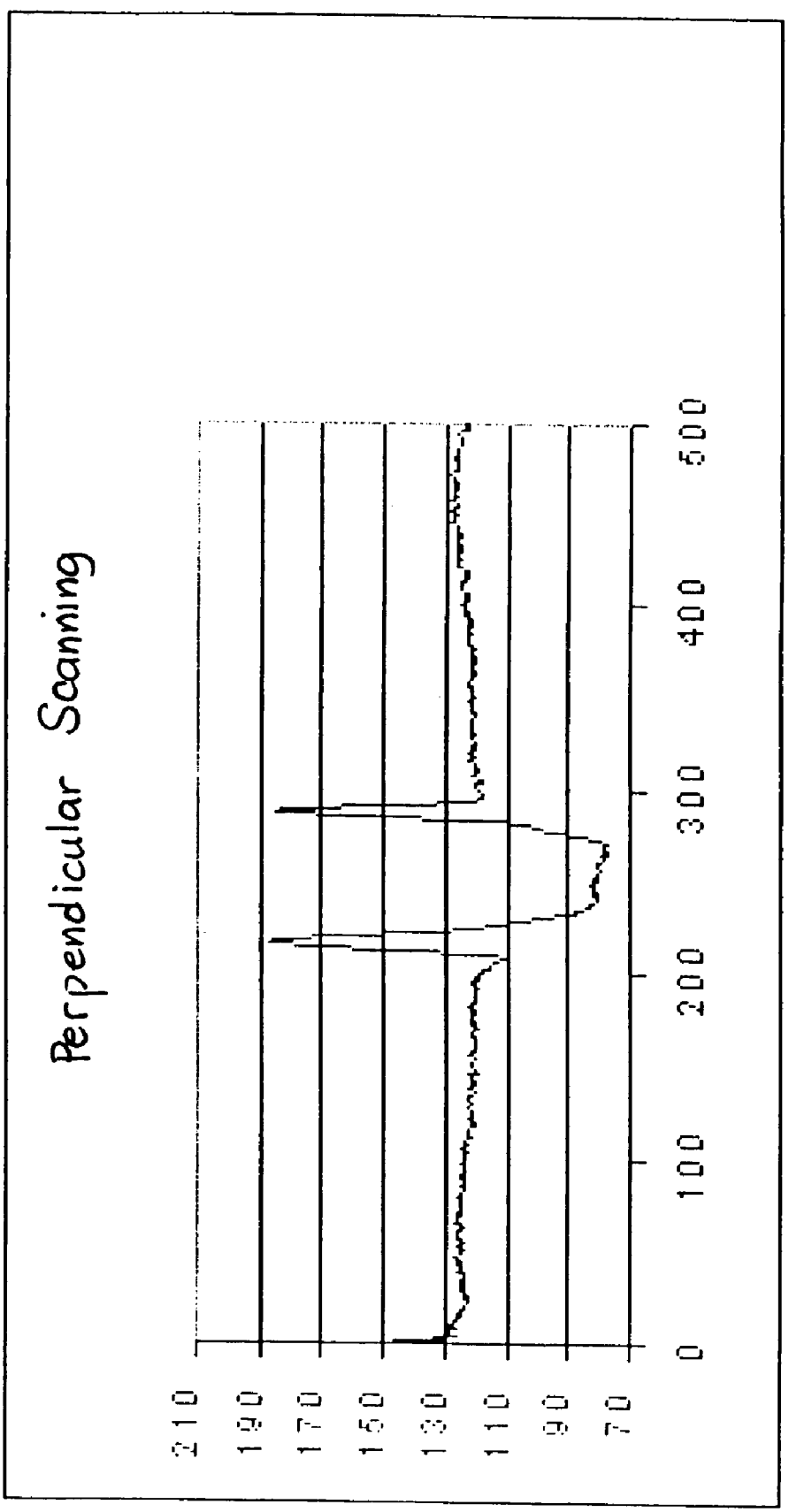
FIG. 3a is a graph showing the edge profiles under a perpendicular scanning method.
Figure 3B:
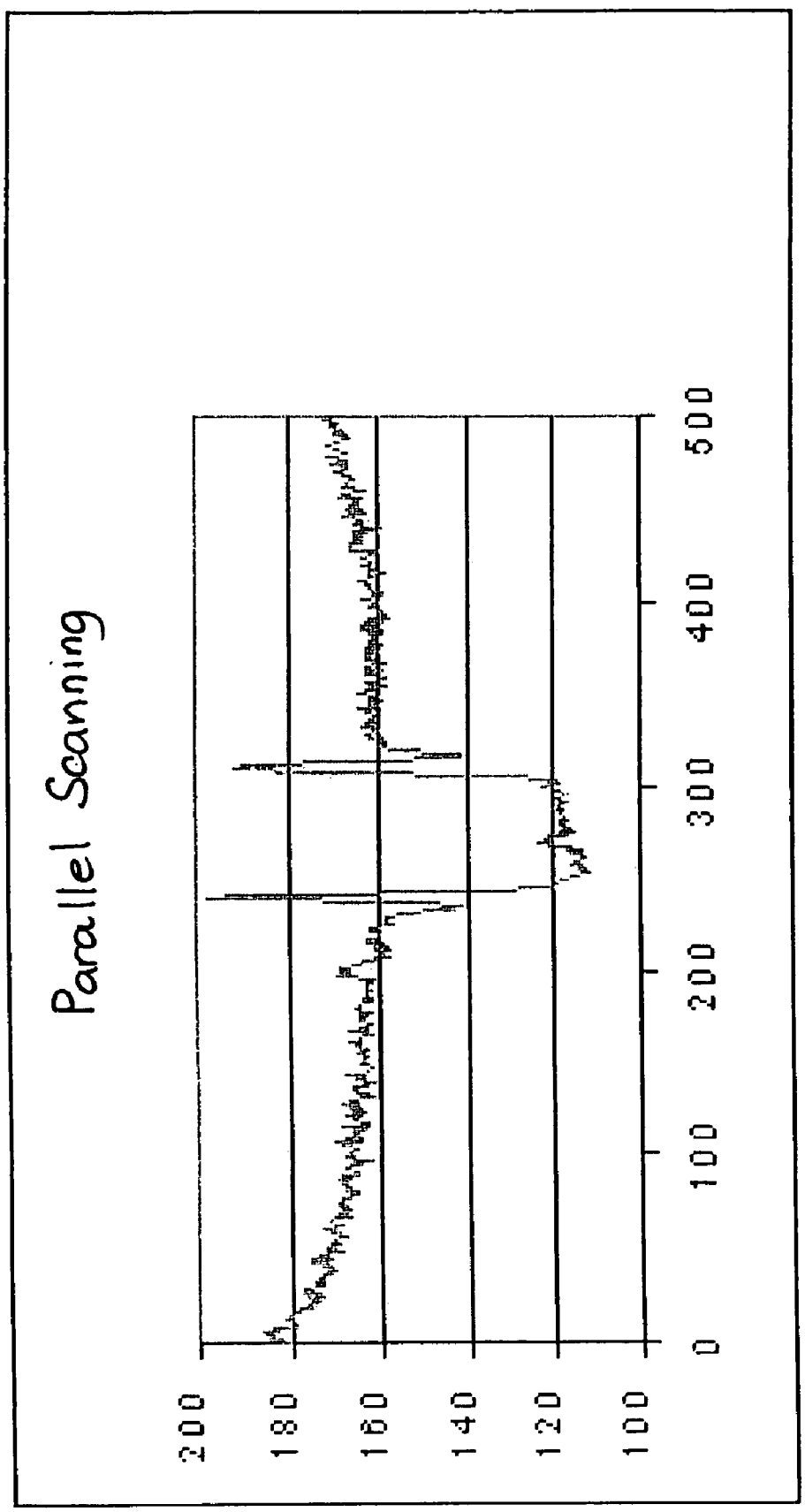
FIG. 3b is a graph showing the edge profiles under a parallel scanning method.

FIG. 3a is a graph showing the experimental edge profiles under a perpendicular scanning method. The y-axis of the graph indicates intensity, and the x-axis indicates position along a horizontal scan line in FIG. 1 (a). FIG. 3b is a graph showing the experimental edge profiles under a parallel scanning method. Here, the y-axis of the graph indicates intensity, and the x-axis indicates position along a horizontal scan line in FIG. 1 (b). Comparing FIG. 3a with FIG. 3b shows that the edge profiles under the parallel scanning (FIG. 3b) are advantageously narrower.

Figure 4:
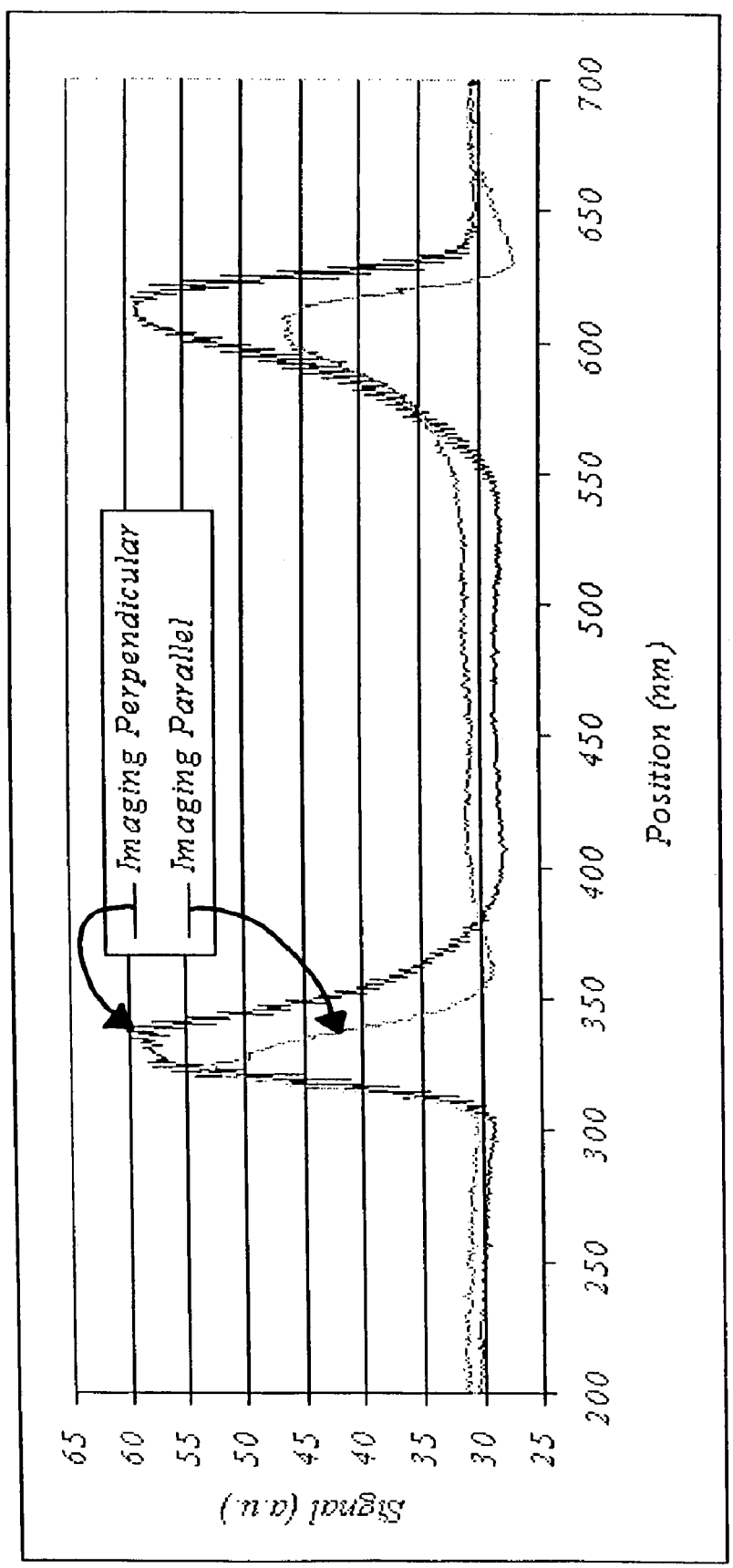
FIG. 4 is a graph directly comparing the experimental edge profiles under the perpendicular and parallel scanning methods.

FIG. 4 is a graph directly comparing the experimental edge profiles under the perpendicular and parallel scanning methods. The edge profiles from the parallel scanning (Imaging Parallel) are shown to be advantageously narrower than the edge profiles under the perpendicular scanning (Imaging Perpendicular). Note that the data in FIG. 4 shows an "asymmetrical" effect as follows. The data was collected with the parallel scanning proceeding from left to right. As seen in the figure, the left edge profile is substantially sharper (narrower) than the right edge profile. In other words, there is less edge blurring seen in the data for the edge encountered first as the scan lines proceed from left to right. On the other hand, if the scan lines proceeded from right to left, then the right edge profile would be substantially sharper than the left edge profile. Applicants believe that this asymmetrical effect (where the first encountered edge has less blur) is due to a form of charge build-up.

Figure 5:
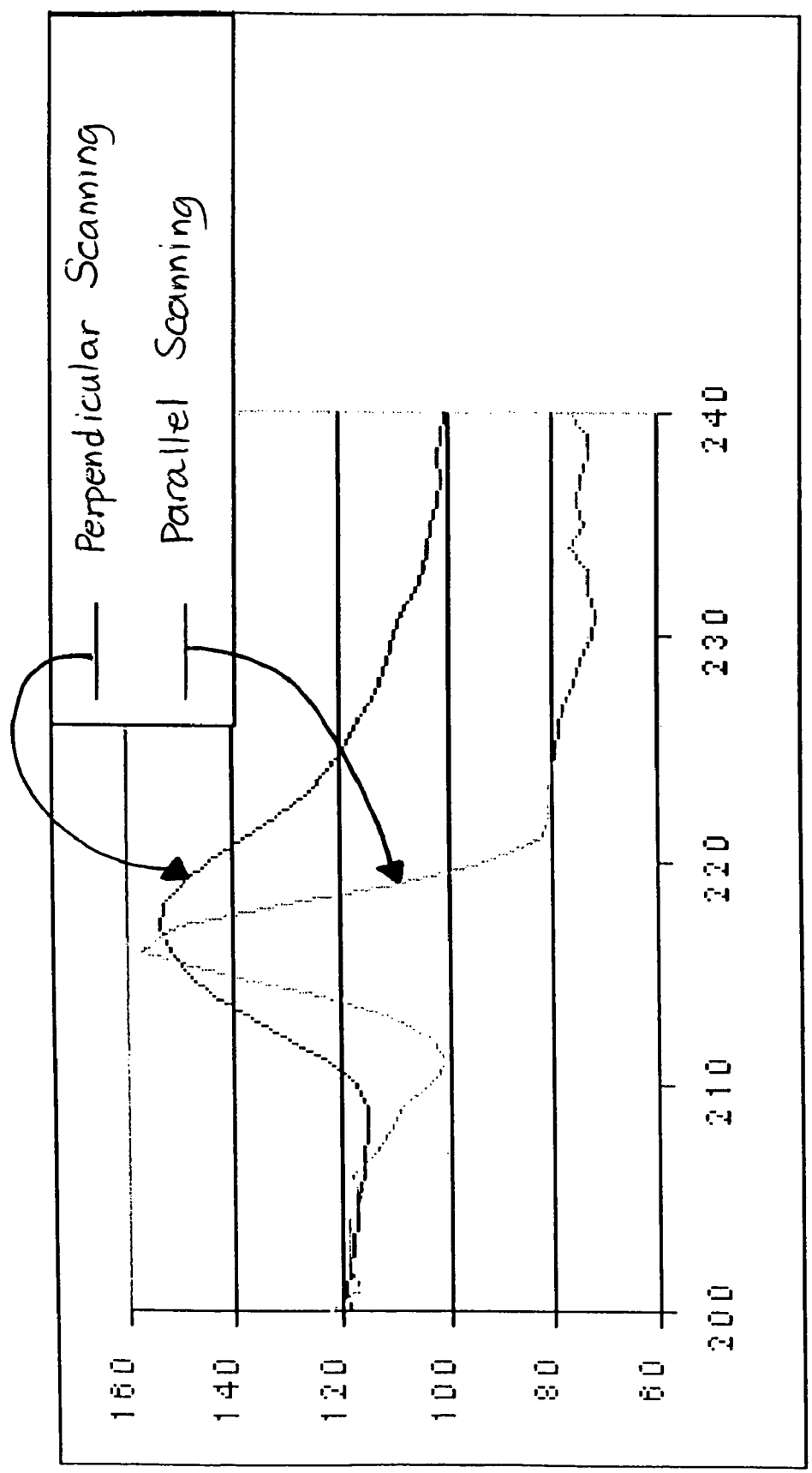
FIG. 5 is a graph comparing in a close-up manner an experimental edge profile under the perpendicular scanning method with that under the parallel scanning method.

FIG. 5 is a graph comparing in a close-up manner an experimental edge profile under the perpendicular scanning method with that under the parallel scanning method. Again, the edge profile from the parallel scanning is shown to be advantageously narrower than the edge profile under the perpendicular scanning.

In accordance with one embodiment, the e-beam scanning methods of the present invention may be implemented, for example, using the system described below in relation to FIGS. 6 through 9c. FIGS. 6 through 9c describes a scanning electron microscope based system that is configured for measuring critical dimensions. In accordance with other embodiments of the present invention, the e-beam scanning methods may be implemented using an substrate inspection system or a defect review system.

Figure 6:
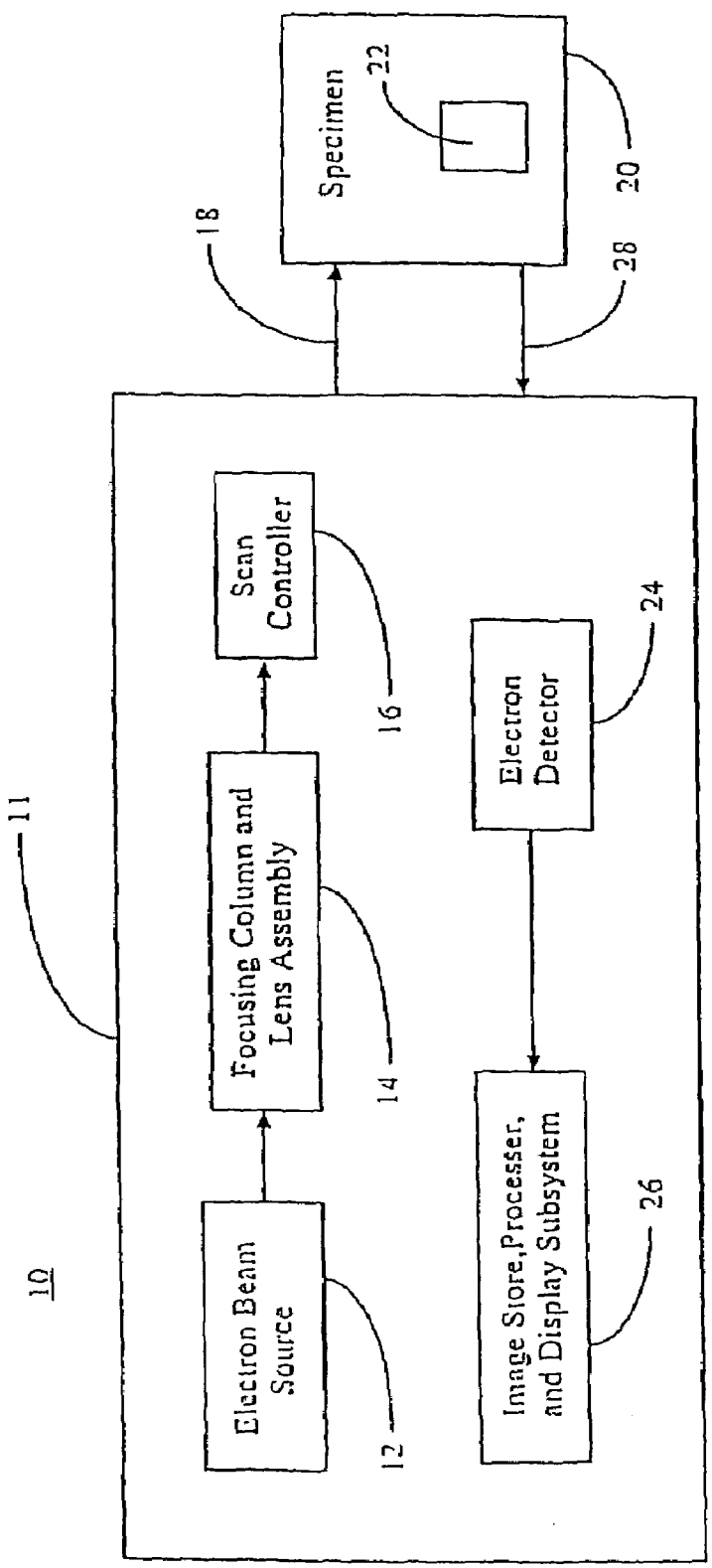
FIG. 6 is a simplified block diagram of a system in accordance with one embodiment of the present invention.

FIG. 6 shows a block diagram of system 10 including an electron microscope subsystem 11 in accordance with one embodiment of the present invention. The electron microscope subsystem 11 includes an electron beam source 12, a focusing column and lens assembly 14, and a scan controller 16 to scan an electron beam across selected regions of specimen 20. Also included in electron microscope system 11 is an electron detector 24 to detect secondary and backscattered electrons from specimen 20. In system 10, electron detector 24 is selected to have a bandwidth that is at least adequate to detect the secondary and backscattered electrons that form electron signal 28. For example, electron detector 24 may be a micro-channel plate, micro-sphere plate, semiconductor diode, or a scintillator/photomultiplier (PMT) assembly, each well known in the art. Then the electrons of signal 28 received by detector 24 are processed and stored for display by image processor and display subsystem 26.

In operation, electron beam 18 is scanned over specimen 20 and secondary and backscattered electron signal 28 is detected by electron detector 24. Further, electron beam 18 is focused on the surface of specimen 20 with the average current into specimen 20 determined by scan controller 16 that controls the raster scanning of beam 18. Electron beam 18, as discussed below, can be scanned for a single frame cycle, and then blanked for a period of one or more frame cycles.

Typically, specimen 20 may be comprised of a variety of materials. Small area 22 of specimen 20 is shown to illustrate a particular area of interest to be scanned to determine features of the specimen in the image of small area 22 developed by image processor and display subsystem 26. For example, small area 22, may, in a degenerate case, be a single line or a single pixel element on specimen 20. The peak current onto small area 22 may be reduced by scanning electron beam 18 faster than the television rate commonly used in conventional SEM instruments. In system 10, electron beam 18 is typically scanned with a line period of 16 microseconds, or four times the rate normally used for TV raster scanning having a line period of 64 microseconds.

Figure 7:
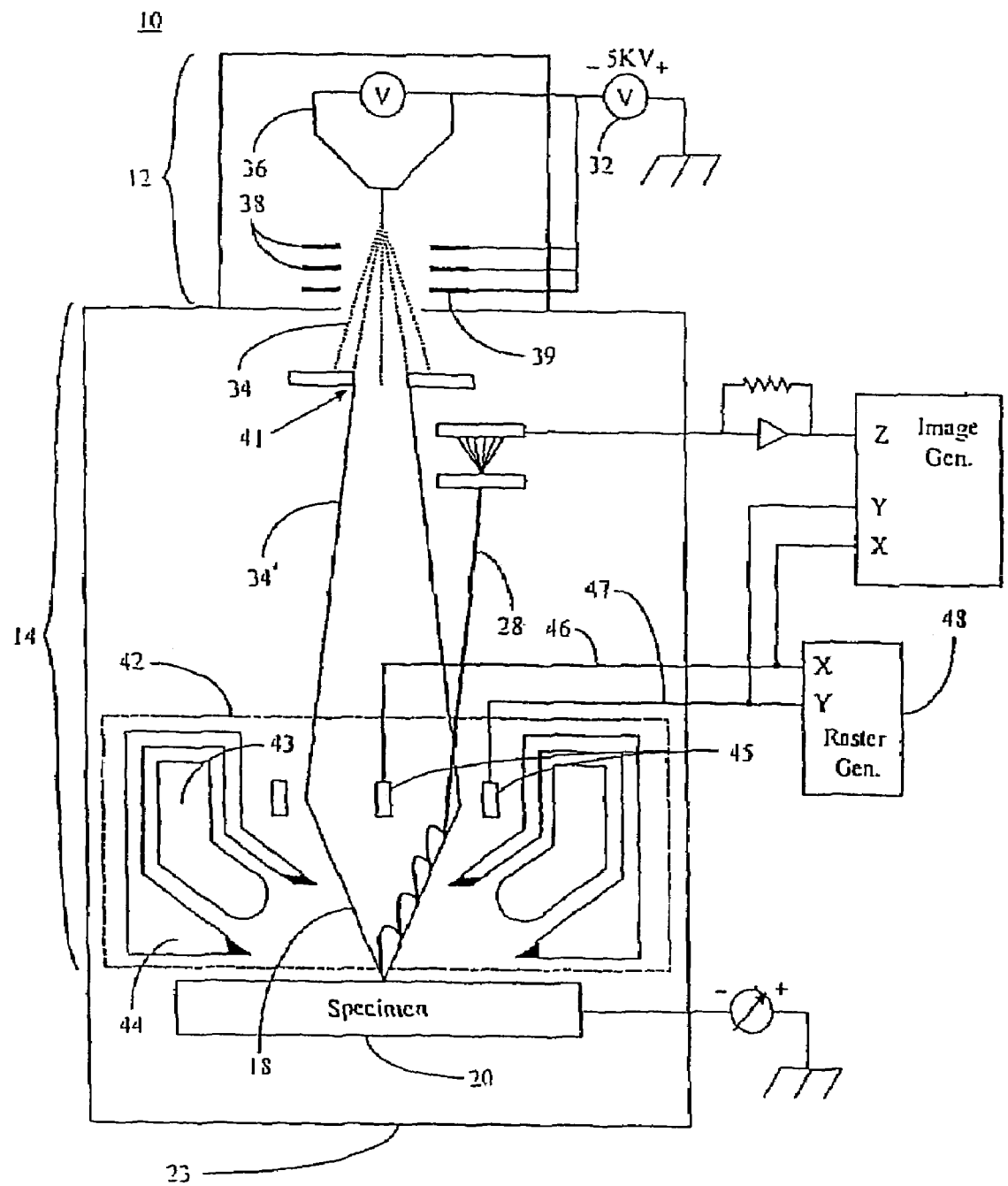
FIG. 7 is a more detailed schematic of the system.

FIG. 7 shows a partial cross-sectional view of electron microscope subsystem 11 to reveal more detail. As shown here, subsystem 11 is shown with electron beam source 12 at the top which produces electron beam 34. One implementation that could be used includes an electron gun 36 that consists of a thermal field emitter (TFE) with the electrons accelerated by a surface field generated by power supply 32. Alternative electron gun embodiments could be employed. The electrons emitted by electron gun 36 are then, within beam source 12, directed through electrodes 38 and gun lens 39 (each also controlled by power supply 32) to form electron beam 34 that enters focusing column and lens assembly 14 to be directed to specimen 20. It should also be noted that electrodes 38 typically include both suppressor and extractor electrodes.

In focusing column and lens assembly 14, electron beam 34 passes through an aperture 41, reducing the beam current from approximately 300 pA to a range of 5 to 100 pA forming what is labelled electron beam 34' in FIG. 7. A larger electron beam current (e.g., 100 pA) is particularly useful for pattern recognition. That larger beam current also reduces the integration time to achieve a given signal-to-noise ratio for the image or linescan which is well known in the art. Stated a little differently, there is a better signal-to-noise ratio for higher beam currents, however there is an improved image quality for lower beam currents.

Electron beam 34' then passes through objective lens 42, including magnetic coils 43 and pole pieces 44, that generate a strong magnetic field. That magnetic field is used to focus beam 34' to form electron beam 18 with a spot size of approximately 5 nm when directed at specimen 20. Additionally, the location of electron beam 18 is controlled with scan plates 45, located within the magnetic field created by coils 43 and pole pieces 44, with scan plates 45 powered by raster generator 48 to direct beam 18 in both the x and y directions across specimen 20 by signals on lines 46 and 47, respectively. To tie FIGS. 6 and 7 together in this area, scan plates 45 and raster generator 48 correspond to scan control 16 in FIG. 6.

Figure 8:
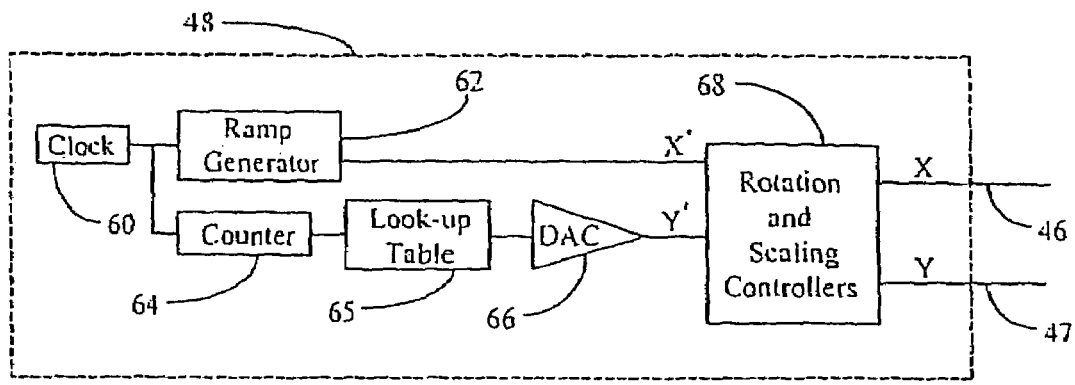
FIG. 8 is an expanded block diagram of the scanning control subsystem in accordance with one embodiment of the present invention.

Referring next to FIG. 8, there is shown a block diagram of one potential embodiment of raster generator 48. Included in this sample embodiment of raster generator 48 is a clock 60 to produce a timing signal that is applied to ramp generator 62 and counter 64. Ramp generator 62 in turn produces a ramp signal x', and counter 64 produces a digital signal which represents a preset count. The preset count from counter 64 being representative of the timing signal from clock 60. In turn, the preset count from counter 64 is applied to look-up table 65 wherein look-up table 65 has been programmed to select individual y-axis lines on the surface of specimen 20 to be scanned that corresponds to the count from counter 64. It should be noted here that the y-axis lines to be scanned may be sequential; non-sequential; selected lines with one or more intermediate lines skipped; selected lines scanned repeatedly; or any combination or order desired for various regions on the surface of specimen 20. The output digital value of look-up table 65 is then applied to digital-to-analog converter (DAC) 66 to produce a stepped signal, y', that corresponds to the y-axis position on specimen 20 to be scanned. Next, signals x' and y' are directed to the rotation and scaling controllers 68 (e.g., utilizing a multiplying D/A converter with a technique that is well known in the art) that produces signals x and y that are applied to scan plates 45 (see FIG. 7) via lines 46 and 47, respectively, to control the actual x and y positions electron beam 18 scans on specimen 20.

Figure 9A:
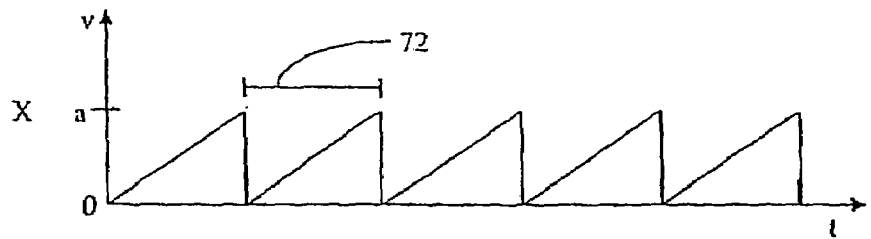
FIGS. 9a-9b show one possible set of scan system voltage control signal waveforms.
Figure 9B:
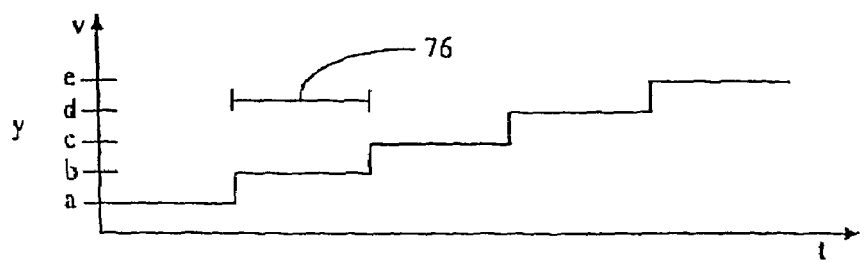
Figure 9C:
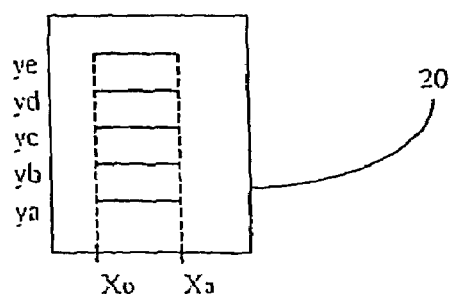
FIG. 9c illustrates the scan pattern on the substrate when the signal waveforms of FIGS. 9a-9b are used.

Referring next to FIGS. 9a and 9b, representative waveforms of signals x (46) and y (47), respectively, from raster generator 48 are shown. In FIG. 9a, ramp segment 72 in the x signal (46) directs beam 18, via scan plates 45, to scan a spot along a single line in the x-axis direction on specimen 20. Since each segment of the signal in FIG. 9a is the same magnitude in voltage, alternatively the same duration in time, the length of each corresponding scan in the x direction is of the same length. Concurrently, in FIG. 9b each step segment 76 of the y signal (47) provides a y-address of a different signal value in the y-axis direction that is traced in the x direction of specimen 20 by the x signal. To illustrate what the x and y signals of FIGS. 9a and 9b are actually causing to happen relative to specimen 20, FIG. 9c is provided to show the paths scanned based on those signals, i.e., each line starts at $x_0$ and proceeds to $x_a$ at each of the corresponding y coordinates starting with $y_a$ and progressing through $y_e$. As described above, FIGS. 9a through 9c serve to illustrate a conventional scan method where the scan lines are horizontal and are scanned in order from bottom to top.

Figure 10:
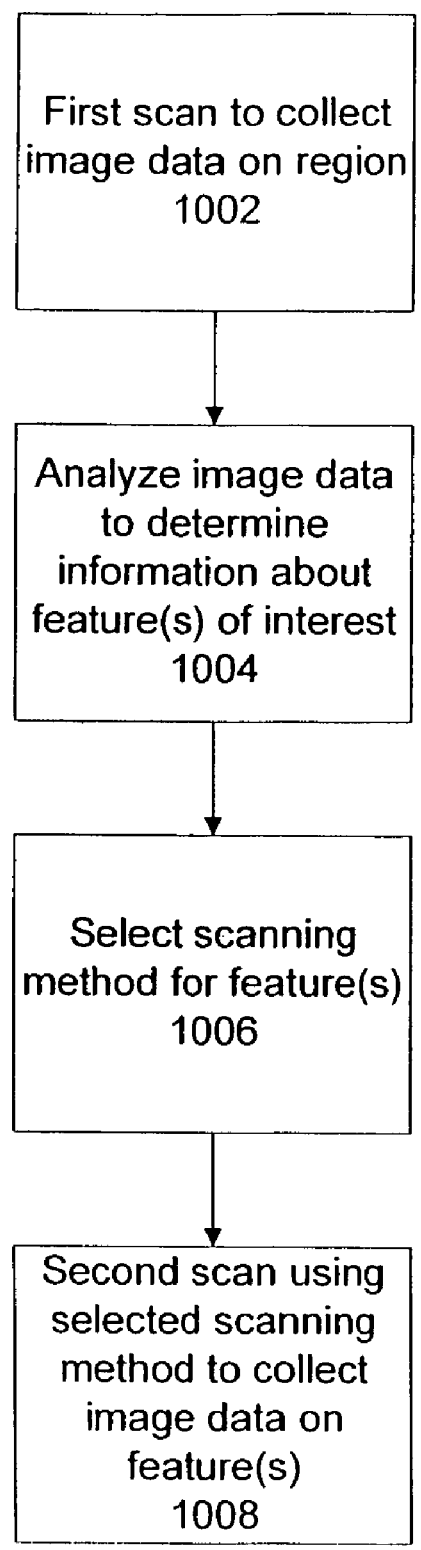
FIG. 10 is a flow chart depicting an adaptive method for e-beam scanning in accordance with an embodiment of the present invention.

FIG. 10 is a flow chart depicting an adaptive method for e-beam scanning in accordance with an embodiment of the present invention. This adaptive method may be utilized to select a scanning method that advantageously reduces the line width blurring in the image data.

A first e-beam scan 1002 is performed to collect image data on a region of a specimen. The first scan 1002 may be performed using a conventional scanning method (which is not adapted to reduce line width blurring). The first scan 1002 may be a rough image scan of the region because, as discussed below, the image data from the first scan is only used to gather information about the feature or features of interest within the region needed to define the scanning strategy for the subsequent scan.

The image data from the first scan 1002 of the region is then analyzed 1004. The analysis 1004 determines the shape and/or orientation of the feature or features of interest within the region. Other information about the feature(s) may also be determined. The analysis 1004 may be performed, for example, using image analysis software configured to make said determination.

With the information determined about the feature(s), an e-beam scanning method is selected 1006 for a second e-beam scan 1008 of the feature(s). The scanning method for the second scan 1008 may be selected so that symmetric parallel scanning (rather than perpendicular scanning) is applied to feature edges of interest.

The second e-beam scan 1008 is then performed using the selected scanning method to collect image data on the feature(s). As discussed above, applicants believe that such parallel scanning should reduce line width blurring at those edges. In accordance with one embodiment, the scan rate of the second scan 1008 would be relatively slower in comparison to that of the first scan 1002 discussed above. The second scan 1008 is used for the actual analysis (metrology, inspection, etc).

The following FIGS. 11-17 illustrate novel scanning methods determined by the applicants to result in less blurring of certain types of feature edges in accordance with embodiments of the present invention. As discussed above, in accordance with the adaptive method of FIG. 10, the scanning method to be utilized may be selected depending upon the shape and/or orientation of the feature of interest. In accordance with another embodiment, some of the scanning methods may be used independent of the shape and/or orientation of the feature of interest.

These scanning methods may be implemented, for example, by appropriate modification to the x and y waveform signals discussed above in relation to FIGS. 9a and 9b.

Other techniques for implementing these scanning methods are within the capability of one of ordinary skill in the pertinent art.

Note that in the following figures the spacing of the scan lines is shown as wide apart for purposes of illustration and explanation. In actual use, the scan lines would be much denser (closer together). Similarly, for purposes of illustration and explanation, the number of the scan lines shown is shown as much fewer than would actually be used.

Figure 11A:
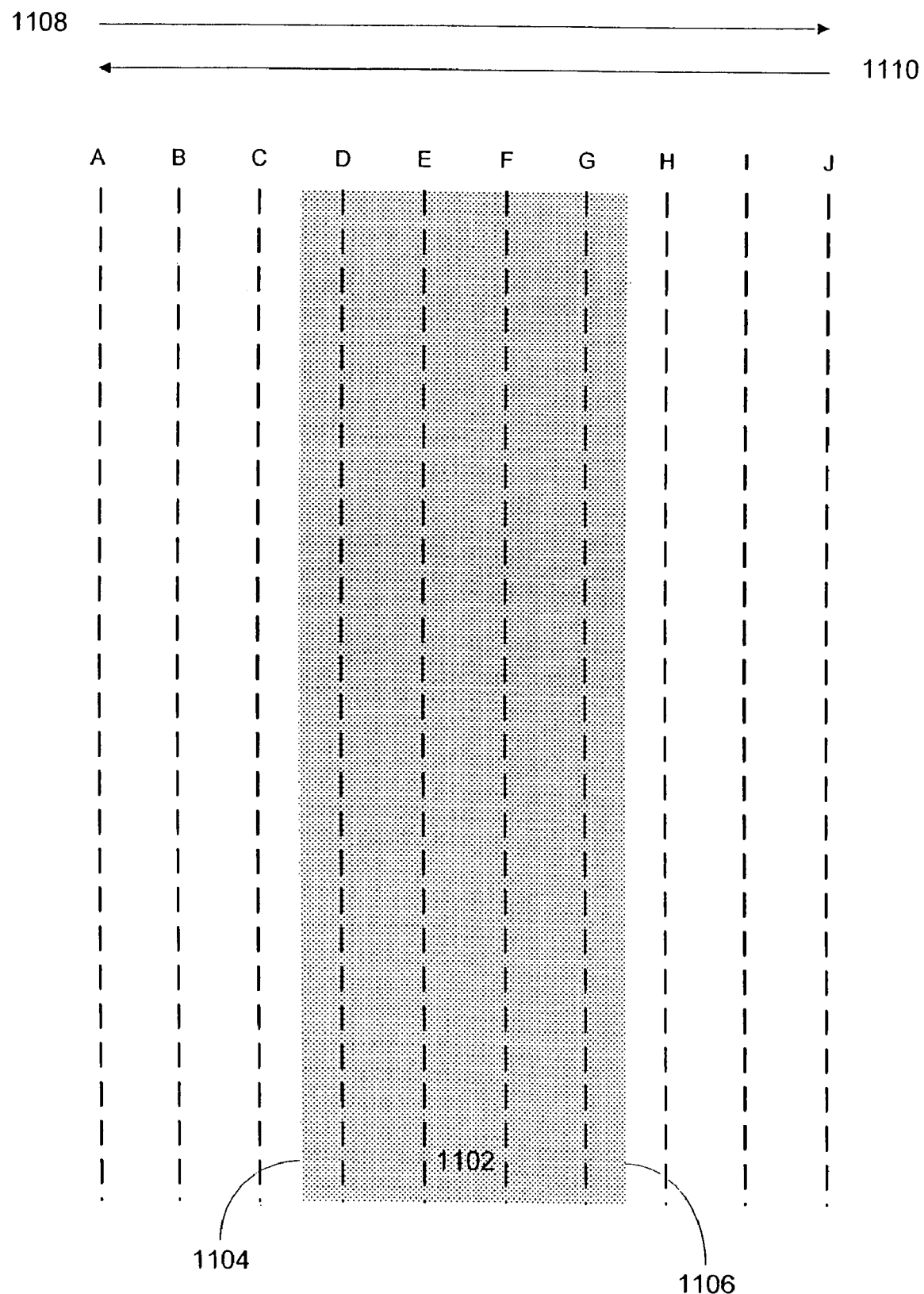
FIG. 11a is a diagram depicting a first bi-directional linear e-beam scanning method in accordance with an embodiment of the present invention.

FIG. 11a is a diagram depicting a first bi-directional linear e-beam scanning method in accordance with an embodiment of the present invention. In this example, the feature of interest 1102 is vertically oriented, with a left edge 1104 and a right edge 1106. The scanning method of FIG. 11a uses parallel (in this example, vertical) scan lines that go from a first side to a second side, then go in reverse from the second side back to the first side. In the particular case shown in FIG. 11a, the parallel scan lines first proceed from left to right 1108 (A, B, C, D, E, F, G, H, I, then J), then proceed from right to left 1110 (J, I, H, G, F, E, D, C, B, then A). Of course, as mentioned above, the scan lines in actual use will be much more dense than illustrated.

Advantageously, the scanning method illustrated by FIG. 11a should result in sharper (less blurred) edges in the resultant image data. First, the parallel scanning with respect to the feature edges will result in sharper feature edges. Second, by scanning in both directions (bi-directionally), applicants believe that the scanning method of FIG. 11a mitigates the asymmetrical effect discussed above in relation to FIG. 4.

Figure 11B:
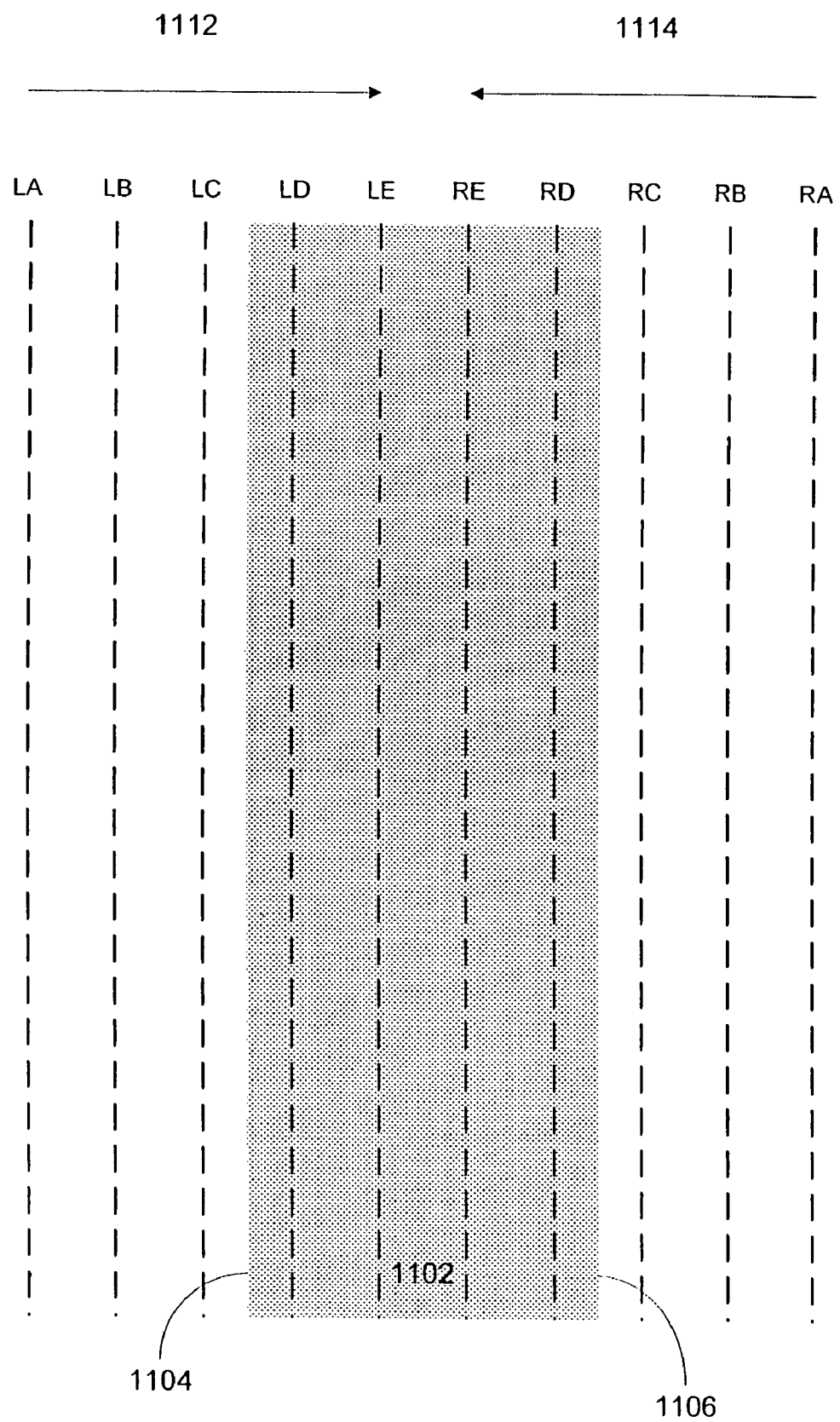
FIG. 11b is a diagram depicting a second bi-directional linear e-beam scanning method in accordance with an embodiment of the present invention.

FIG. 11b is a diagram depicting a second bi-directional linear e-beam scanning method in accordance with an embodiment of the present invention. Here, again, the feature of interest 1102 in this example is vertically oriented, with a left edge 1104 and a right edge 1106. The scanning method of FIG. 11b uses parallel (in this example, vertical) scan lines that go towards the middle portion of the feature of interest 1102. In one embodiment, a first series of lines (LA, LB, LC, LD, then LE) are scanned 1112 from the left to the middle portion of the feature 1102, then a second series of scan lines (RA, RB, RC, RD, then RE) are scanned 1114 from the right to the middle portion of the feature 1102. As depicted, the scanning would thus proceed in this order: LA, LB, LC, LD, LE, RA, RB, RC, RD, then RE. (Of course, in another embodiment, a first series of lines would be scanned 1114 from the right to the middle portion of the feature 1102, then a second series of scan lines would be scanned 1112 from the left to the middle portion of the feature 1102.)

Advantageously, the scanning method illustrated by FIG. 11b should result in sharper (less blurred) edges in the resultant image data. First, the parallel scanning with respect to the feature edges will result in sharper feature edges. Second, by scanning from one side to the middle, then from the other side to the middle, applicants believe that the scanning method of FIG. 11b may avoid the asymmetrical blurring discussed above in relation to FIG. 4.

Figure 12:
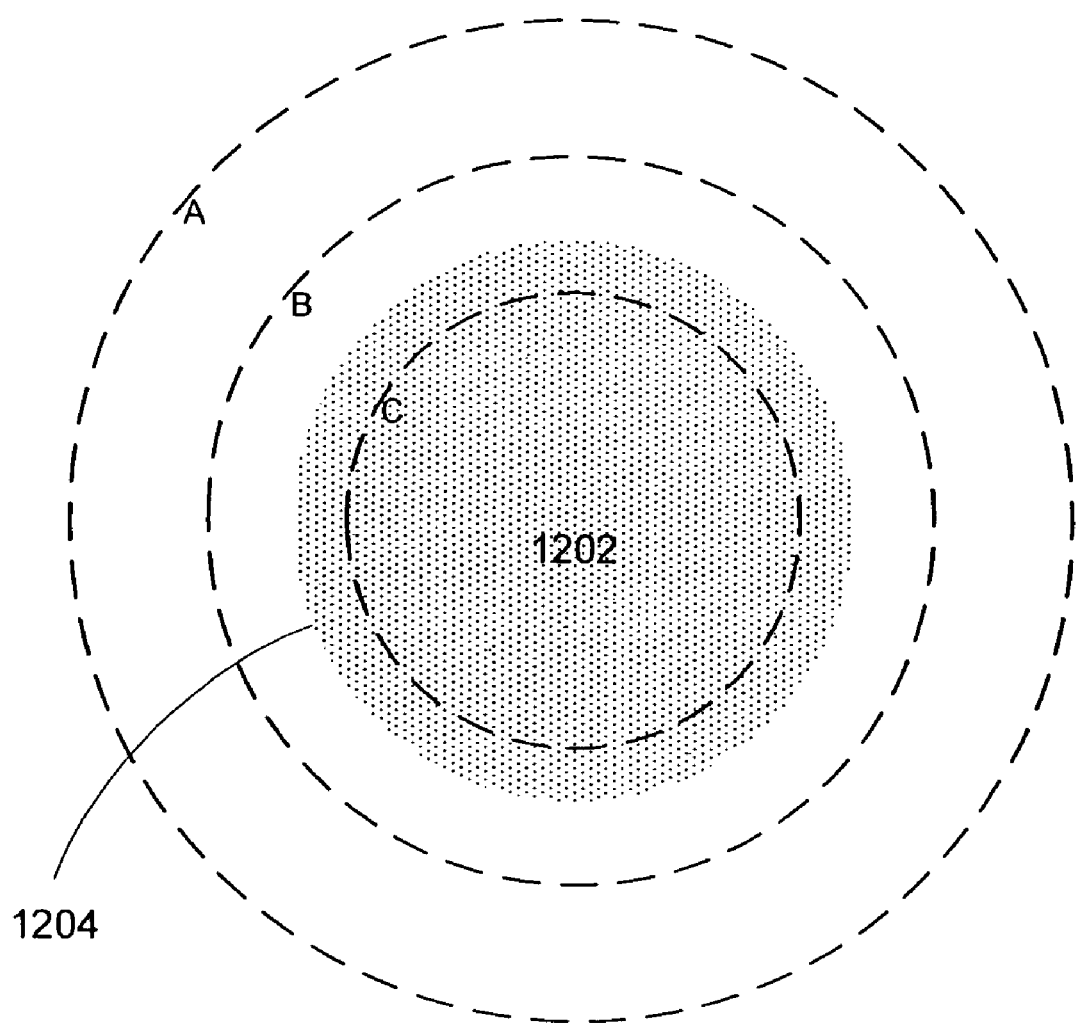
FIG. 12 is a diagram depicting a concentric convergent e-beam scanning method in accordance with an embodiment of the present invention.

FIG. 12 is a diagram depicting a concentric convergent e-beam scanning method in accordance with an embodiment of the present invention. In this example, the feature of interest 1202 on the specimen is circularly shaped with a circularly shaped feature edge 1204. The scanning method of FIG. 12 uses concentric scan lines (A, B, C) that converge towards the middle portion of the feature of interest 1202. As depicted, first circle A would be scanned, then circle B, then circle C.

The scanning method illustrated by FIG. 12 should also advantageously result in sharper (less blurred) edges in the resultant image data. The concentric scanning with respect to the feature edge is a form of parallel scanning that will result in sharper feature edges.

Figure 13:
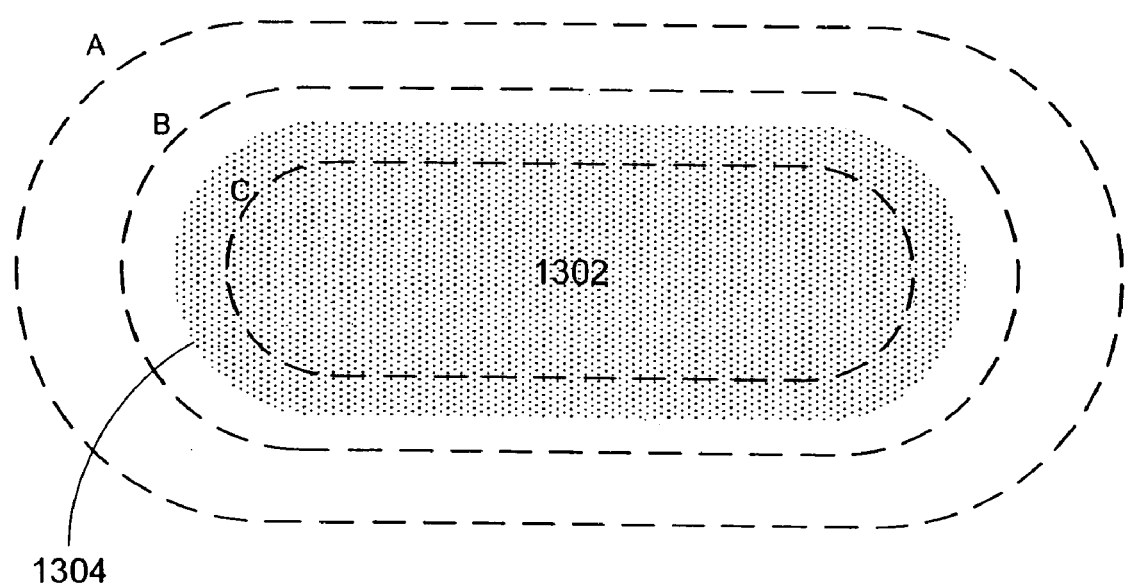
FIG. 13 is another diagram depicting a convergent e-beam scanning method in accordance with an embodiment of the present invention.

FIG. 13 is another diagram depicting a convergent e-beam scanning method in accordance with an embodiment of the present invention. This example is used to show that the feature of interest 1302 on the specimen does not have to be line or circularly shaped. Rather, an arbitrary-shaped feature with a feature edge 1304 may be converged upon in accordance with an embodiment of the invention. In other words, this scanning method should work with shapes that vary from the particular one shown in FIG. 13. The scanning method of FIG. 13 uses scan lines (A, B, C) that converge towards the middle portion of the feature of interest 1302. As depicted, first line A would be scanned, then line B, then line C.

The scanning method illustrated by FIG. 13 should also advantageously result in sharper (less blurred) edges in the resultant image data. The convergent scanning with respect to the feature edge 1304 is a form of parallel scanning that will result in sharper feature edges.

Figure 14:
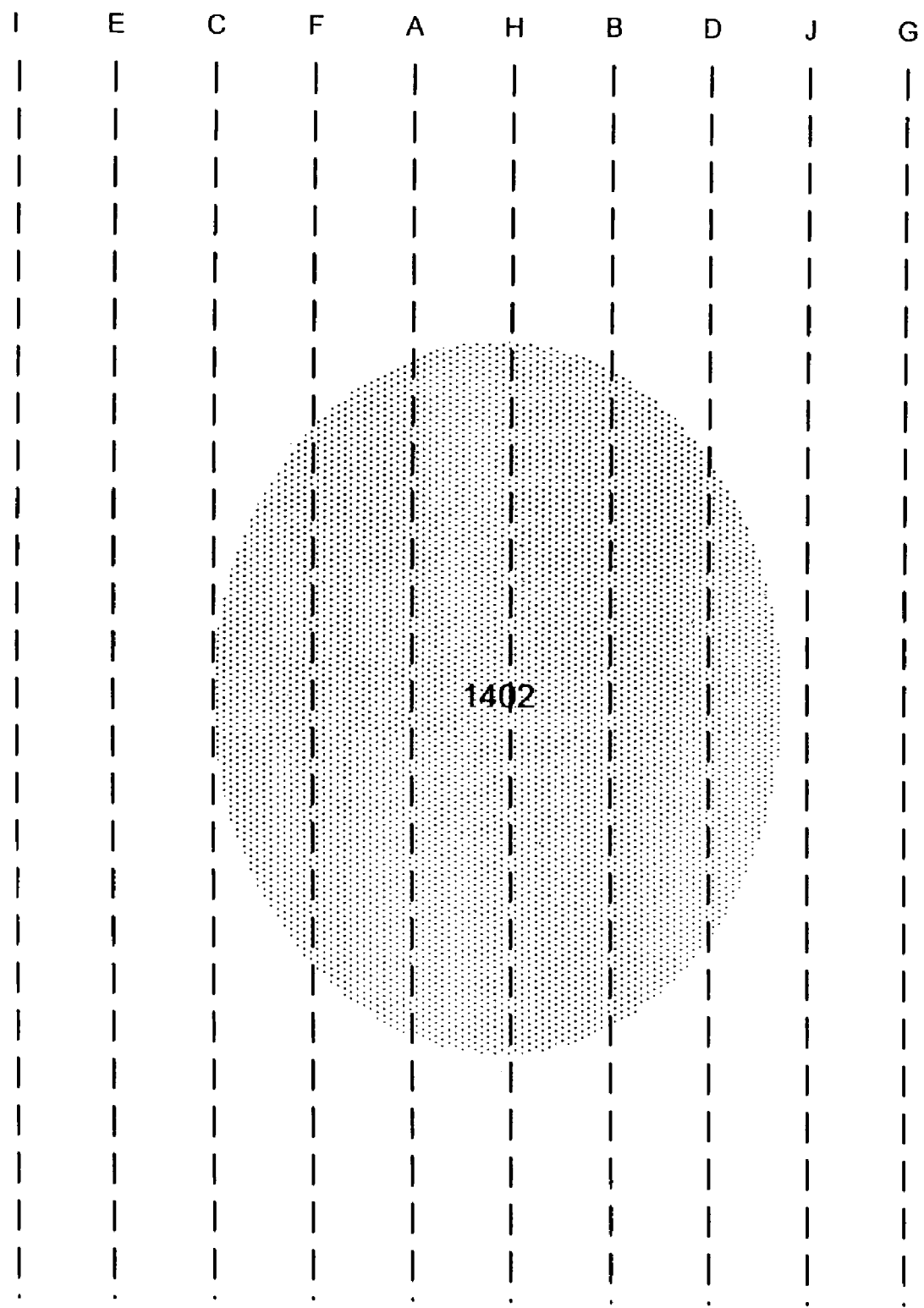
FIG. 14 is a diagram depicting a random linear e-beam scanning method in accordance with an embodiment of the present invention.
Figure 15:
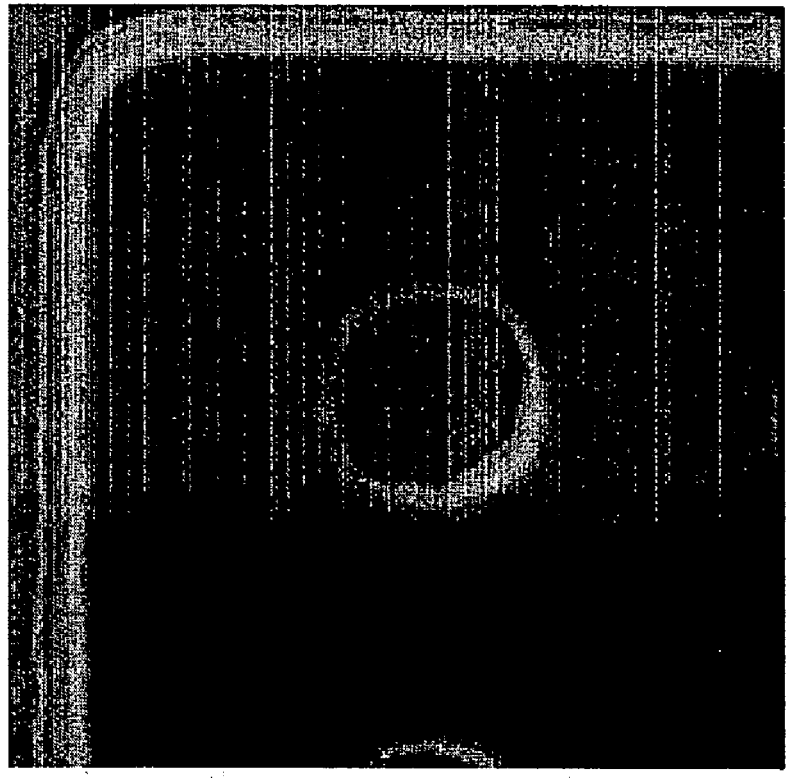
FIG. 15 is an example of the effects of random scanning.
Figure 15:
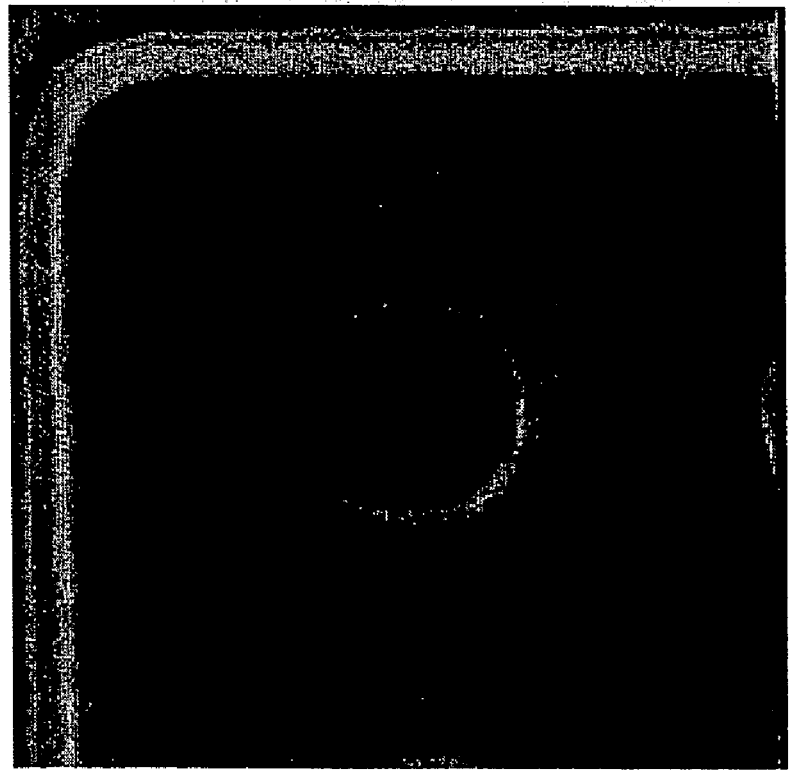

FIG. 14 is a diagram depicting a random linear e-beam scanning method in accordance with an embodiment of the present invention. In this example, the feature of interest 1402 is oval or ellipsoidal, but this random scanning method should be applicable to a variety of feature shapes. In this method, the order of the scan lines are random or pseudo-random. In the example illustrated, the order in which the lines are scanned is: A, B, C, D, E, F, G, H, I, then J. As shown in FIG. 14, this ordering of the lines is random in nature. Applicants believe that such a random scanning method advantageously modify the effect of charge build-up. An example of the effect of random scanning is shown in FIG. 15.

Figure 16A:
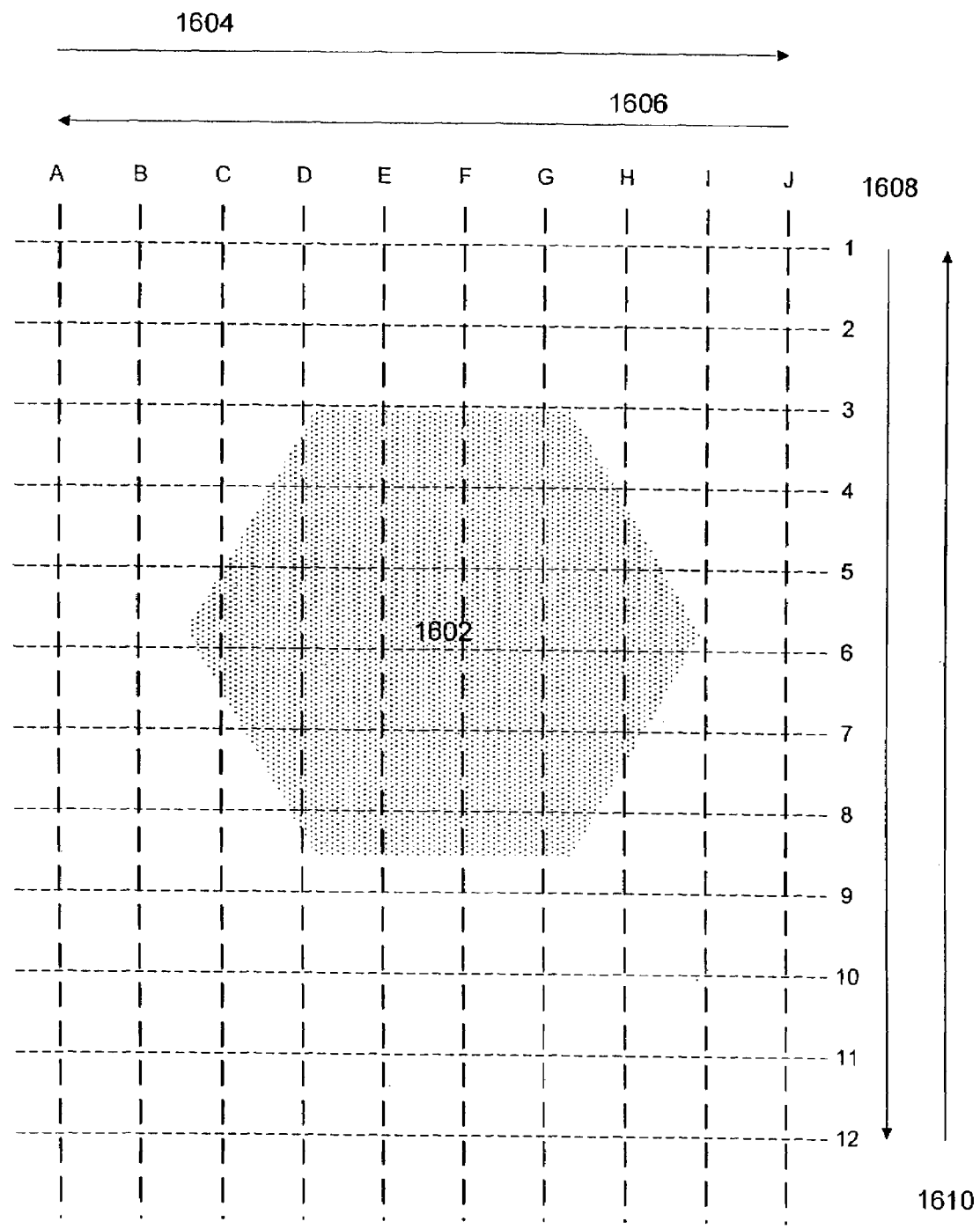
FIG. 16a is a diagram depicting a two-dimensional bi-directional e-beam scanning method in accordance with an embodiment of the present invention.

FIG. 16a is a diagram depicting a two-dimensional bi-directional e-beam scanning method in accordance with an embodiment of the present invention. In this example, the feature of interest 1602 is hexagonal, but this scanning method should be applicable to a variety of feature shapes. In the particular embodiment shown in FIG. 16a, the scan lines first proceed to the right 1604 (A, B, C, D, E, F, G, H, I, then J), then proceed to the left 1606 (J, I, H, G, F, E, D, C, B, then A); then proceed down 1608 (1, 2, 3, 4, 5, 6, 7, 8, 9, 10, 11, then 12); then proceed up 1610 (12, 11, 10, 9, 8, 7, 6, 5, 4, 3, 2, then 1). In other embodiments, the order may vary. For example, the scan lines may first proceed left 1606, then right 1604, then up 1610, then down 1608. As another example, the scan lines may first proceed down 1608, then right 1604, then up 1610, the left 1606. Other embodiments would be other permutations. In other embodiments the scan lines proceed using a general sequence of angles, rather than restricted to orthogonal directions. Applicants believe that such a two-dimensional bi-directional scanning method advantageously reduces the edge blurring by reducing the effect of charge build-up.

Figure 16B:
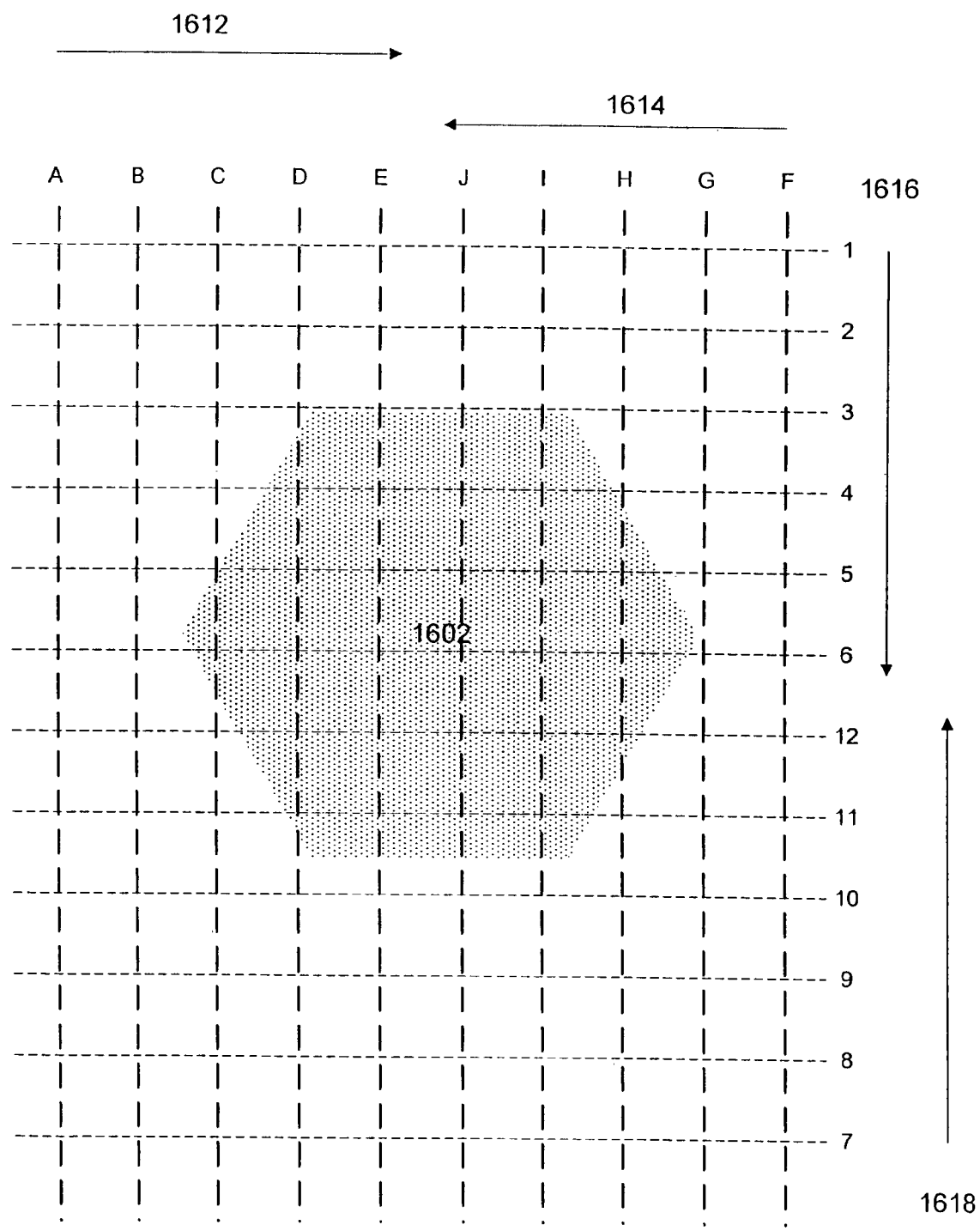
FIG. 16b is a diagram depicting a two-dimensional linear convergent e-beam scanning method in accordance with an embodiment of the present invention.

FIG. 16b is a diagram depicting a two-dimensional linear convergent e-beam scanning method in accordance with an embodiment of the present invention. Again, the feature of interest 1602 is hexagonal in this example, but this scanning method should be applicable to a variety of feature shapes. In the particular embodiment shown in FIG. 16b, the scan lines first proceed from right to middle 1612 (A, B, C, D, then E), then proceed from left to middle 1614 (J, I, H, G, then F); then proceed from top to middle 1616 (1, 2, 3, 4, then 5); then proceed from bottom to middle 1618 (12, 11,

10, 9, 8, then 7). In other embodiments, the order may vary. For example, the scan lines may first proceed from right to middle 1614, then left to middle 1612, then from bottom to middle 1618, then from top to middle 1616. Other embodiments would be other permutations. In other embodiments the scan lines proceed using a general sequence of angles, rather than restricted to orthogonal directions. Applicants believe that such a two-dimensional bi-directional scanning method advantageously reduces the edge blurring by reducing the effect of charge build-up.

Figure 17:
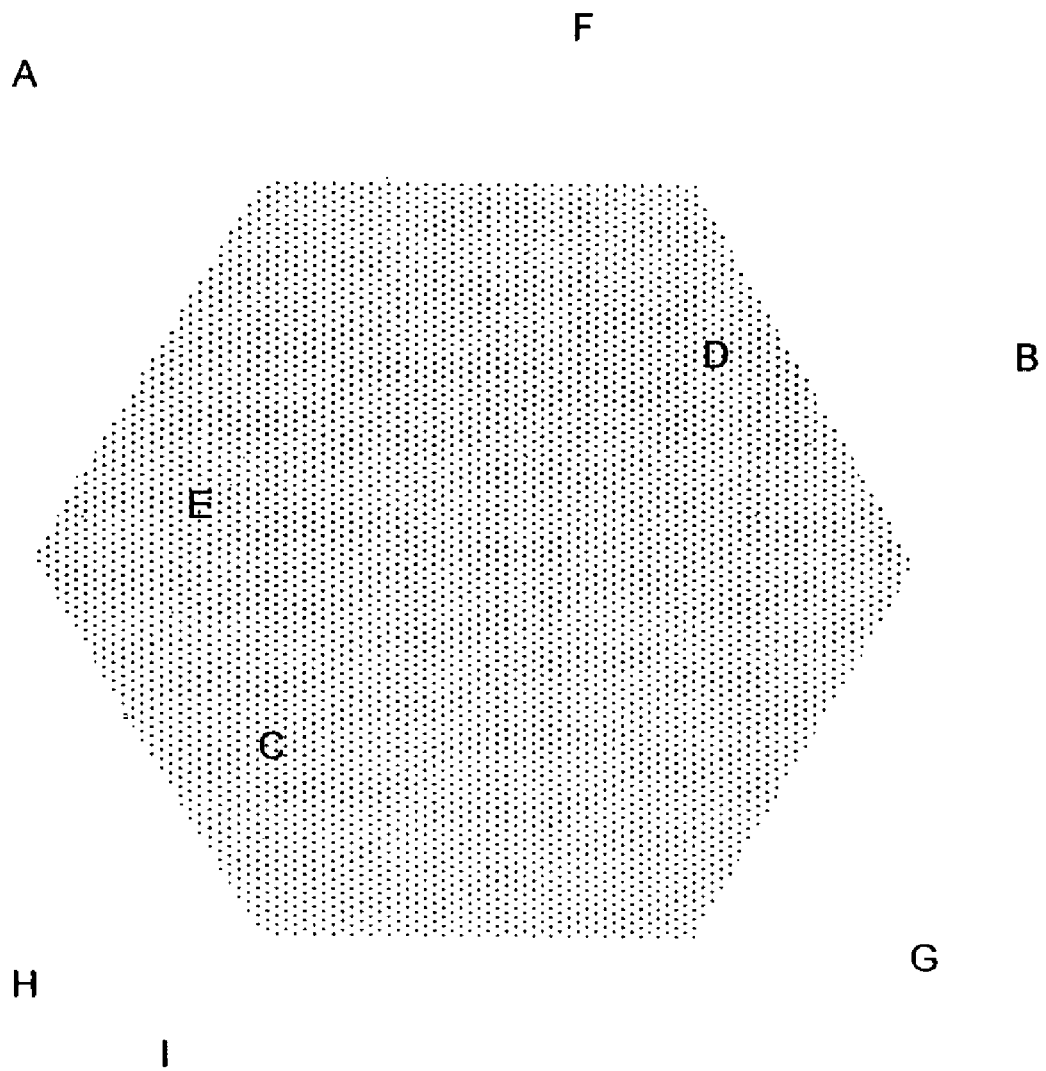
FIG. 17 is a diagram depicting a random pixel e-beam scanning method in accordance with an embodiment of the present invention.

FIG. 17 is a diagram depicting a random pixel e-beam scanning method in accordance with an embodiment of the present invention. Again, the feature of interest is hexagonal in this example, but this random pixel scanning method should be applicable to a variety of feature shapes. In this method, the order in which the pixels are scanned is random or pseudo-random. In the example illustrated, the order in which the pixels are scanned is: A, B, C, D, E, F, G, H, then I, and so on. Of course, there are many more pixels to be scanned then shown in the illustration. As shown in FIG. 17, this ordering of the pixels is random in nature. In one embodiment, the next pixel scanned in a frame may be selected from a group of unscanned pixels in that frame. Applicants believe that such a random pixel scanning method advantageously modifies the effect of charge build-up.

Figure 18:
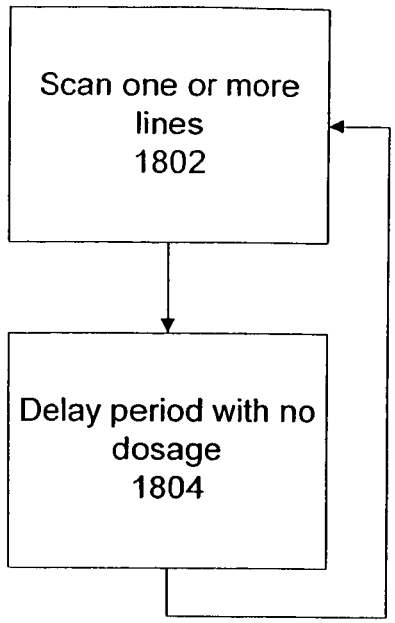
FIG. 18 is a flow chart depicting a delayed line-based e-beam scanning method in accordance with an embodiment of the present invention.

FIG. 18 is a flow chart depicting a delayed line-based e-beam scanning method in accordance with an embodiment of the present invention. Here, one or more lines are scanned 1802, then a delay period 1804 is introduced during which no electron dosage impacts the specimen. Applicants believe that this line-based e-beam scanning method advantageously modifies the effect of charge build-up.

Figure 19:
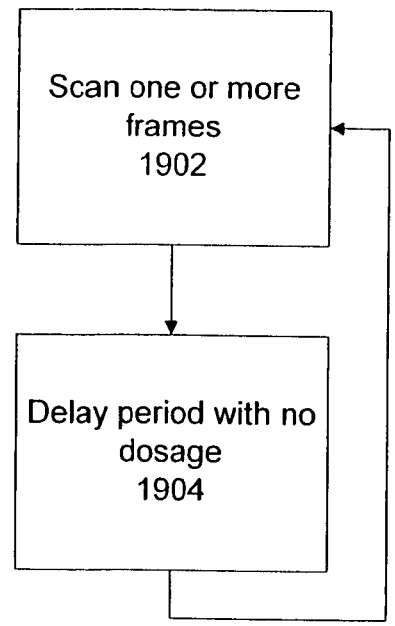
FIG. 19 is a flow chart depicting a delayed frame-based e-beam scanning method in accordance with an embodiment of the present invention.

FIG. 19 is a flow chart depicting a delayed frame-based e-beam scanning method in accordance with an embodiment of the present invention. Here, one or more frames are scanned 1902, then a delay period 1904 is introduced during which no electron dosage impacts the specimen. Such a delay period in between frames effectively reduces the overall electron dosage absorbed by the specimen. Applicants believe that this frame-based e-beam scanning method also advantageously modifies the effect of charge build-up.

Figure 20:
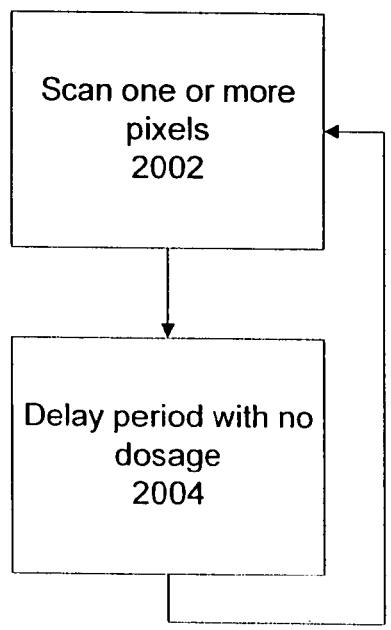
FIG. 20 is a flow chart depicting a delayed pixel-based e-beam scanning method in accordance with an embodiment of the present invention.

FIG. 20 is a flow chart depicting a delayed pixel-based e-beam scanning method in accordance with an embodiment of the present invention. Here, one or more pixels are scanned 2002, then a delay period 2004 is introduced during which no electron dosage impacts the specimen. Such a delay period in between pixel scans effectively reduces the overall electron dosage absorbed by the specimen. Applicants believe that this pixel-based e-beam scanning method also advantageously modifies the effect of charge build-up.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of electron beam scanning for generating image data, the method comprising:
   a first scan on a region to collect first image data;
   processing the first image data to determine information about a line feature in the region, wherein the line feature includes two edge features;
   using the information determined from the first image data to select a scanning pattern for imaging with scan lines parallel to the two edge features; and
   a second scan using the selected scanning pattern to collect second image data,
   wherein the selected scanning pattern comprises a bi-directional linear scanning pattern in which a sequence of scan lines parallel to the two edge features progress in a first direction perpendicular to the scan lines, then progress in a second direction opposite to the first direction, and
   further wherein the sequence of scan lines proceeds in each direction towards a middle of and not through said line feature.

2. The method of claim 1, wherein scanning lines parallel to the two edge features results in less blurring of the edge features in the second image data.

3. A method of electron beam scanning for generating image data, the method comprising:
   a first scan on a region to collect first image data;
   processing the first image data to determine information about a line feature in the region, wherein the line feature includes two edge features;
   using the information determined from the first image data to select a scanning pattern for imaging with scan lines parallel to the two edge features; and
   a second scan using the selected scanning pattern to collect second image data,
   wherein the selected scanning pattern comprises a bi-directional linear scanning pattern in which a sequence of scan lines parallel to the two edge features progress in a first direction perpendicular to the scan lines, then progress in a second direction opposite to the first direction,
   further wherein the region includes a rectangular feature, and wherein the selected scanning pattern comprises a two-dimensional bi-directional scanning pattern.

4. The method of claim 3, wherein the two-dimensional scanning pattern includes scan lines proceeding in each direction through said rectangular feature.

5. The method of claim 3, wherein the two-dimensional scanning pattern includes scan lines proceeding in each direction towards a middle and not through said rectangular feature.

6. A method of electron beam scanning for measurement, inspection or review of a semiconductor substrate, the method comprising imaging a line feature on the substrate, selecting an orientation of scan lines so that the scan lines are parallel to edges of the line feature, scanning bi-directionally in that a first series of the scan lines proceeds in a first direction perpendicular to the scan lines and a second series of the scan lines proceeds in a second direction perpendicular to the scan lines, and scanning bi-directionally in two dimensions in that a third series of scan lines proceeds in a third direction and a fourth series of scan lines proceeds in a fourth direction, wherein the first and second directions are opposite from each other, and further wherein the third and fourth directions are perpendicular to the first and second directions.

7. A system of electron beam scanning for measurement, inspection or review, the system comprising:
   means for a first scan on a region to collect first image data;
   means for processing the first image data to determine information about a line feature in the region, wherein the line feature comprises two edge features;
   means for using the information determined from the first image data to select a scanning pattern for imaging with scan lines parallel to the two edge features; and
   means for a second scan using the selected scanning pattern to collect second image data,
   wherein the selected scanning pattern comprises a bi-directional linear scanning pattern in which a sequence of scan lines parallel to the two edge features progress in a first direction perpendicular to the scan lines, then progress in a second direction opposite to the first direction, and
   further wherein the sequence of scan lines proceeds in each direction towards a middle of and not through said line feature.

* * * * *